(12) United States Patent
Hingston et al.

(10) Patent No.: US 11,648,135 B2
(45) Date of Patent: May 16, 2023

(54) COATED STENT

(71) Applicant: BOSTON SCIENTIFIC SCIMED, INC., Maple Grove, MN (US)

(72) Inventors: John Hingston, Framingham, MA (US); Laura Elizabeth Christakis, Framingham, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 479 days.

(21) Appl. No.: 16/127,707

(22) Filed: Sep. 11, 2018

(65) Prior Publication Data

US 2019/0076274 A1 Mar. 14, 2019

Related U.S. Application Data

(60) Provisional application No. 62/558,046, filed on Sep. 13, 2017.

(51) Int. Cl.
| | | |
|---|---|---|
| *A61F 2/82* | (2013.01) | |
| *A61L 31/08* | (2006.01) | |
| *A61L 31/00* | (2006.01) | |
| *A61F 2/90* | (2013.01) | |
| *A61L 31/14* | (2006.01) | |
| *A61F 2/04* | (2013.01) | |
| *A61L 31/18* | (2006.01) | |

(52) U.S. Cl.
CPC ............... *A61F 2/82* (2013.01); *A61F 2/90* (2013.01); *A61L 31/005* (2013.01); *A61L 31/08* (2013.01); *A61L 31/14* (2013.01); *A61L 31/148* (2013.01); *A61F 2/04* (2013.01); *A61F 2210/0004* (2013.01); *A61F 2210/0076* (2013.01); *A61F 2230/001* (2013.01); *A61F 2240/001* (2013.01); *A61F 2250/0039* (2013.01); *A61F 2250/0098* (2013.01); *A61L 31/18* (2013.01)

(58) Field of Classification Search
CPC .................................. A61F 2/82; A61L 31/08
See application file for complete search history.

(56) References Cited

U.S. PATENT DOCUMENTS

| 6,051,750 A | 4/2000 | Bell |
|---|---|---|
| 6,096,070 A | 8/2000 | Ragheb et al. |
| (Continued) | | |

FOREIGN PATENT DOCUMENTS

| EP | 2365007 B1 | 2/2015 |
|---|---|---|
| WO | 2007044026 A2 | 4/2007 |
| (Continued) | | |

OTHER PUBLICATIONS

Frantz et al., "The Extracellular Matrix At A Glance," Journal of Cell Science, 6 pages, 2010.
(Continued)

*Primary Examiner* — Matthew W Schall
(74) *Attorney, Agent, or Firm* — Seager, Tufte & Wickhem, LLP

(57) ABSTRACT

An implantable medical device may comprise an elongated tubular body having a scaffolding forming a plurality of cells. A polymeric covering may be disposed over at least a portion of the stent. The covering may include a plurality of voids formed in an outer surface thereof. An extracellular matrix material coating may be disposed over the polymeric covering and within the plurality of voids.

20 Claims, 8 Drawing Sheets

(56) References Cited

U.S. PATENT DOCUMENTS

| | | |
|---|---|---|
| 6,599,928 B2 | 7/2003 | Kunz et al. |
| 6,872,439 B2 | 3/2005 | Fearing et al. |
| 7,223,286 B2 | 5/2007 | Wright et al. |
| 7,615,373 B2 | 11/2009 | Simpson et al. |
| 7,959,942 B2 | 6/2011 | Cottone |
| 8,221,783 B2 | 7/2012 | Helmus et al. |
| 8,283,414 B2 | 10/2012 | Yu et al. |
| 8,529,956 B2 | 9/2013 | Campbell et al. |
| 8,574,612 B2 | 11/2013 | Edelman |
| 8,613,776 B2 | 12/2013 | Cheung et al. |
| 8,691,321 B2 | 4/2014 | Cottone |
| 8,703,168 B2 | 4/2014 | Flanagan et al. |
| 8,834,578 B2 | 9/2014 | Bayon et al. |
| 9,198,999 B2 | 12/2015 | Hall et al. |
| 9,629,713 B2 | 4/2017 | Frendl et al. |
| 9,655,710 B2 | 5/2017 | Eller et al. |
| 9,688,741 B2 | 6/2017 | Annabi et al. |
| 2002/0095219 A1 | 7/2002 | Nelles et al. |
| 2003/0211135 A1 | 11/2003 | Greenhalgh et al. |
| 2005/0110214 A1 | 5/2005 | Shank et al. |
| 2005/0149175 A1 | 7/2005 | Hunter et al. |
| 2005/0165467 A1 | 7/2005 | Hunter et al. |
| 2005/0255230 A1 | 11/2005 | Clerc et al. |
| 2005/0256564 A1 | 11/2005 | Yang et al. |
| 2006/0085063 A1 | 4/2006 | Shastri et al. |
| 2006/0228389 A1 | 10/2006 | Li et al. |
| 2007/0269481 A1 | 11/2007 | Li et al. |
| 2007/0293927 A1 | 12/2007 | Frank et al. |
| 2008/0033522 A1* | 2/2008 | Grewe .................. A61L 31/082 623/1.11 |
| 2008/0287342 A1 | 11/2008 | Yu et al. |
| 2009/0069904 A1 | 3/2009 | Picha |
| 2009/0076595 A1 | 3/2009 | Lindquist et al. |
| 2009/0098176 A1 | 4/2009 | Helmus et al. |
| 2009/0130372 A1 | 5/2009 | Fukui et al. |
| 2009/0138070 A1 | 5/2009 | Holzer et al. |
| 2009/0143855 A1 | 6/2009 | Weber et al. |
| 2009/0187240 A1 | 7/2009 | Clerc et al. |
| 2010/0076555 A1 | 3/2010 | Marten et al. |
| 2010/0241214 A1 | 9/2010 | Holzer et al. |
| 2011/0021965 A1 | 1/2011 | Karp et al. |
| 2011/0111031 A1 | 5/2011 | Jiang et al. |
| 2012/0035715 A1 | 2/2012 | Robida et al. |
| 2012/0141562 A1 | 6/2012 | Achneck et al. |
| 2013/0013083 A1 | 1/2013 | Blum et al. |
| 2013/0085565 A1 | 4/2013 | Eller et al. |
| 2013/0110255 A1 | 5/2013 | Picha et al. |
| 2013/0116405 A1 | 5/2013 | Yu et al. |
| 2013/0218262 A1 | 8/2013 | Ishii et al. |
| 2013/0231753 A1 | 9/2013 | Liddy et al. |
| 2013/0268063 A1 | 10/2013 | Firstenberg et al. |
| 2014/0067047 A1 | 3/2014 | Eller et al. |
| 2014/0074219 A1 | 3/2014 | Hingston et al. |
| 2014/0079758 A1 | 3/2014 | Hall et al. |
| 2014/0081414 A1 | 3/2014 | Hall et al. |
| 2014/0086971 A1 | 3/2014 | Hall et al. |
| 2014/0148846 A1 | 5/2014 | Pereira et al. |
| 2014/0248418 A1 | 9/2014 | Eller et al. |
| 2014/0249619 A1 | 9/2014 | Eller et al. |
| 2014/0277395 A1 | 9/2014 | Firstenberg et al. |
| 2014/0277443 A1 | 9/2014 | Fleury et al. |
| 2015/0045876 A1 | 2/2015 | Clerc et al. |
| 2015/0051693 A1* | 2/2015 | Bertolino .............. B29C 66/742 623/1.13 |
| 2015/0068676 A1 | 3/2015 | Geitz et al. |
| 2015/0086607 A1 | 3/2015 | Johnson et al. |
| 2015/0111308 A1 | 4/2015 | Yu et al. |
| 2015/0258253 A1 | 9/2015 | Fater |
| 2015/0282955 A1 | 10/2015 | Guler et al. |
| 2015/0283308 A1 | 10/2015 | Chutka |
| 2015/0342760 A1 | 12/2015 | Christakis et al. |
| 2015/0359622 A1 | 12/2015 | Matheny |
| 2016/0067741 A1 | 3/2016 | Weiss et al. |
| 2016/0287416 A1 | 10/2016 | Weber |

FOREIGN PATENT DOCUMENTS

| | | | |
|---|---|---|---|
| WO | 2010048281 | A1 | 4/2010 |
| WO | 2011019401 | A2 | 2/2011 |
| WO | 2013040544 | A2 | 3/2013 |
| WO | 2014063194 | A1 | 1/2014 |
| WO | 2014085592 | A1 | 6/2014 |
| WO | 2017004598 | A1 | 1/2017 |

OTHER PUBLICATIONS

Geckil et al., "Engineering Hydrogels As Extracellular Matrix Mimics," National Institute of Health, 29 pages, Apr. 2010.

Yue, "Biology of the Extracellular Matrix: An Overview," J. Glaucoma, (23): 4 pages, 2014.

Badylak et al., "Reprint of: Extracellular Matrix As A Biological Scaffold Material: Structure and Function," Acta Biomaterialia, 10 pages, 2008.

Swinehart et al., "Extracellular Matrix Bioscaffolds In Tissue Remodeling and Morphogenesis," Developmental Dynamics, 10 pages, 2016.

Vowden, et al., "Effect of Amelogenin Extracellular Matrix Protein (Xelma) as an Adjunct Treatment to High Compression in Hard-to-Heal Venous Leg Ulcers: a Multi-Centre, Randomised Controlled Trial," Vascular Unit, Bradford Royal Infirmary, Molnlycke Health Care, May 2-4, 2007, 3 pages.

* cited by examiner

COATED STENT

CROSS-REFERENCE TO RELATED APPLICATIONS

This application claims priority under 35 U.S.C. § 119 to U.S. Provisional Application Ser. No. 62/558,046, filed Sep. 13, 2017, the entirety of which is incorporated herein by reference.

TECHNICAL FIELD

The present disclosure pertains to medical devices, and methods for manufacturing medical devices. More particularly, the present disclosure pertains to mucosal adhesive coated stents and methods for coating stents.

BACKGROUND

Implantable stents are devices that are placed in a body structure, such as a blood vessel, esophagus, trachea, biliary tract, colon, intestine, stomach or body cavity, to provide support and to maintain the structure open. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

SUMMARY

This disclosure provides design, material, manufacturing method, and use alternatives for medical devices. An example medical device may include a stent.

In a first example, an implantable medical device may comprise an elongated tubular body having a scaffolding forming a plurality of cells, a polymeric covering disposed over at least a portion of the scaffolding, wherein the covering includes a plurality of voids formed in an outer surface thereof, and an extracellular matrix material coating disposed over the polymeric covering and within the plurality of voids.

Alternatively, or additionally, in another example, the outer surface of the polymeric covering may comprise a micropatterned surface including a plurality of protrusions with the plurality of voids defined therebetween.

Alternatively, or additionally, in another example, the plurality of protrusions may be formed as a monolithic structure with the polymeric covering.

Alternatively, or additionally, in another example, the polymeric covering may include a first layer and a second layer radially outward of the first layer, the second layer including the micropatterned outer surface having the plurality of protrusions with the plurality of voids defined therebetween.

Alternatively, or additionally, in another example, the second layer may be adhesively secured to the first layer.

Alternatively, or additionally, in another example, the first layer may extend from a first end to a second end of the elongated tubular body and the second layer may extend along less than an entire length of the first layer.

Alternatively, or additionally, in another example, the second layer may be disposed over a first region of the first layer adjacent the first end of the elongated tubular body.

Alternatively, or additionally, in another example, the second layer may be disposed over a second region of the first layer adjacent the second end of the elongated tubular body, with an intermediate portion of the first layer uncovered by the second layer.

Alternatively, or additionally, in another example, the elongated tubular body and the polymeric covering may be bioabsorbable.

Alternatively, or additionally, in another example, the extracellular matrix material may form a continuous outer coating over the entire outer surface of the polymeric covering.

In another example, a method of manufacturing an implantable medical device may comprise disposing a polymeric covering over an elongated tubular body having a scaffolding forming a plurality of cells, the polymeric covering including a plurality of voids, applying a liquid extracellular matrix hydrogel over the polymeric covering and within the plurality of voids, and drying the extracellular matrix hydrogel to form an extracellular matrix material.

Alternatively, or additionally, in another example, disposing the polymeric covering over the elongated tubular body may comprise molding the polymeric coating over the scaffolding.

Alternatively, or additionally, in another example, molding the polymeric coating over the scaffolding may further comprise molding a micropattern including a plurality of protrusions and the plurality of voids in an outer surface of the polymeric covering.

Alternatively, or additionally, in another example, disposing the polymeric covering over the elongated tubular body may comprise electro-spin coating a polymer material over the scaffolding.

Alternatively, or additionally, in another example, the elongated tubular body and the polymeric covering may be bioabsorbable.

In another example, an implantable medical device may comprise an elongated tubular body having a scaffolding forming a plurality of cells, a polymeric covering disposed over at least a portion of the stent, wherein the covering includes a plurality of voids formed in an outer surface thereof, and an extracellular matrix material coating disposed over the polymeric covering and within the plurality of voids.

Alternatively, or additionally, in another example, the outer surface of the polymeric covering may comprise a micropatterned surface including a plurality of protrusions with the plurality of voids defined therebetween.

Alternatively, or additionally, in another example, the plurality of protrusions may be formed as a monolithic structure with the polymeric covering.

Alternatively, or additionally, in another example, the polymeric covering may include a first layer and a second layer radially outward of the first layer, the second layer including the micropatterned outer surface having the plurality of protrusions with the plurality of voids defined therebetween.

Alternatively, or additionally, in another example, the second layer may be adhesively secured to the first layer.

Alternatively, or additionally, in another example, the first layer may extend from a first end to a second end of the elongated tubular body and the second layer may extend along less than an entire length of the first layer.

Alternatively, or additionally, in another example, the second layer may be disposed over a first region of the first layer adjacent the first end of the elongated tubular body.

Alternatively, or additionally, in another example, the second layer may be disposed over a second region of the first layer adjacent the second end of the elongated tubular body, with an intermediate portion of the first layer uncovered by the second layer.

Alternatively, or additionally, in another example, the elongated tubular body and the polymeric covering may be bioabsorbable.

Alternatively, or additionally, in another example, the extracellular matrix material may form a continuous outer coating over the entire outer surface of the polymeric covering.

In another example, a method of manufacturing an implantable medical device may comprise applying a polymeric covering over an elongated tubular body having a scaffolding forming a plurality of cells, the polymeric covering having an outer surface including a micropattern having a plurality of protrusions and a plurality of voids defined therebetween, applying a liquid extracellular matrix hydrogel over at least a portion of the polymeric covering and within the plurality of voids, and drying the extracellular matrix hydrogel to form an extracellular matrix material.

Alternatively, or additionally, in another example, applying the polymeric covering over the elongated tubular body may comprise spray coating, electro-spin coating, dip coating, or injection molding the polymeric coating over the scaffolding.

Alternatively, or additionally, in another example, applying the liquid extracellular matrix hydrogel may comprise dip coating.

Alternatively, or additionally, in another example, applying the liquid extracellular matrix hydrogel may comprise spray coating.

Alternatively, or additionally, in another example, the elongated tubular body and the polymeric covering may be bioabsorbable.

In another example, a method of manufacturing an implantable medical device may comprise applying a polymeric covering over an elongated tubular body having a scaffolding forming a plurality of cells, the polymeric covering having an outer surface including a plurality of voids, applying a liquid extracellular matrix hydrogel over the polymeric covering and within the plurality of voids, and drying the extracellular matrix hydrogel to form an extracellular matrix material on the outer surface of the polymer covering.

Alternatively, or additionally, in another example, disposing the polymeric covering over the elongated tubular body may comprise electro-spin coating a polymer material over the scaffolding.

Alternatively, or additionally, in another example, applying the liquid extracellular matrix hydrogel may comprise dip coating.

Alternatively, or additionally, in another example, applying the liquid extracellular matrix hydrogel may comprise spray coating.

Alternatively, or additionally, in another example, the elongated tubular body and the polymeric covering may be bioabsorbable.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments in connection with the accompanying drawings, in which.

Figure 1:
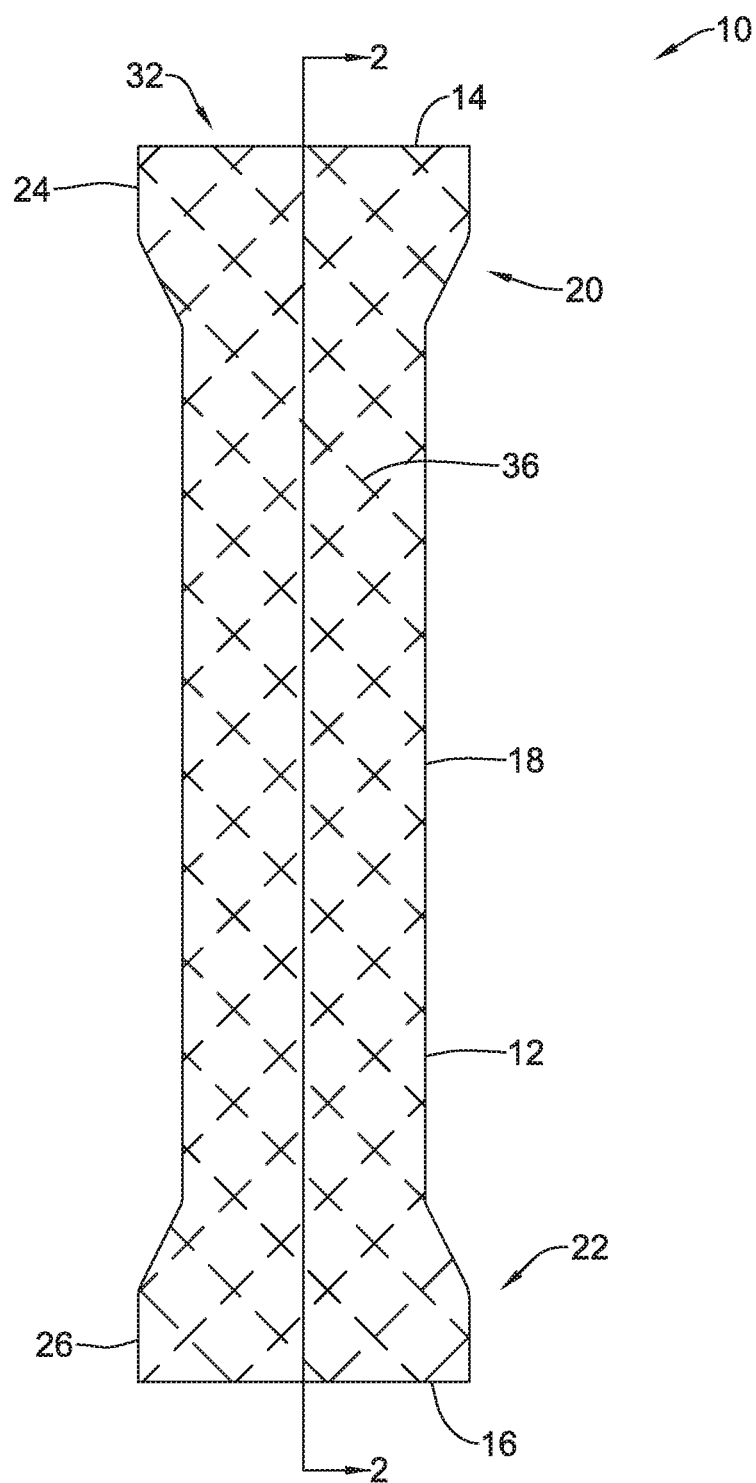
FIG. 1 is a side view of an illustrative stent.

While the disclosure is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may be indicative as including numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

Although some suitable dimensions, ranges, and/or values pertaining to various components, features and/or specifications are disclosed, one of the skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end further from the device operator during use.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with one embodiment, it should be understood that such feature, structure, or characteristic may also be used connection with other embodiments whether or not explicitly described unless cleared stated to the contrary.

In some instances, it may be desirable to provide an endoluminal implant, or stent, that can deliver luminal patency in a patient with an esophageal stricture or other medical condition. Such stents may be used in patients experiencing dysphagia, sometimes due to esophageal cancer. An esophageal stent may allow a patient to maintain nutrition via oral intake during cancer treatment or palliation periods. However, a common complication of gastrointestinal (GI) stents is stent migration due to the peristaltic motion subjected to the stent. It may be desirable to provide a stent that can deliver luminal patency while minimizing migration of the stent. While the embodiments disclosed herein are discussed with reference to esophageal stents, it is contemplated that the stents described herein may be used and sized for use in other locations such as, but not limited to: bodily tissue, bodily organs, vascular lumens, non-vascular lumens and combinations thereof, such as, but not limited to, in the coronary or peripheral vasculature, trachea, bronchi, colon, small intestine, biliary tract, urinary tract, prostate, brain, stomach and the like.

As physicians treat an increasing number of patients with benign conditions, there has been a growing call for removable stents. The removability of a stent may be at odds with measures taken to reduce the risk of stent migration. For example, stents having a generally open braided structure along at least a portion thereof may be used to reduce stent migration. The open structure may provide a scaffold that promotes tissue ingrowth into the stent. The ingrowth of the tissue may anchor the stent in place and reduce the risk of migration. However, tissue ingrowth into the stent may lead to re-occlusion of the lumen (e.g., esophagus) which may necessitate re-intervention. Further, stents anchored by tissue ingrowth may be difficult to move and/or remove without causing trauma to the patient. Covering the open braided structure with, for example, a polymer coating to create a physical barrier between the lumen of the stent and the esophageal wall may reduce occlusion but increase migration rates of the stent. In another example, stents have been provided with a flare or increased diameter at one or both ends thereof. While the flares may reduce migration, the decreased migration rates of coated, flared stents are still not comparable to those of bare metal stents. Therefore it is desirable to provide a stent which maintains luminal patency while also including potential for removability and additionally allowing it to greatly reduce the potential for migration.

While the embodiments disclosed herein are discussed with reference to stents, it is contemplated that the patterns and techniques described herein may be used in other devices, such as, but not limited to, grafts, stent-grafts, vena cava filters, expandable frameworks, etc. It is further contemplated that the devices and methods described herein may be used and sized for use in locations such as, but not limited to: bodily tissue, bodily organs, vascular lumens, non-vascular lumens and combinations thereof, such as, but not limited to, in the coronary or peripheral vasculature, trachea, esophagus, bronchi, colon, small intestine, biliary tract, urinary tract, prostate, brain, stomach and the like.

Figure 2:
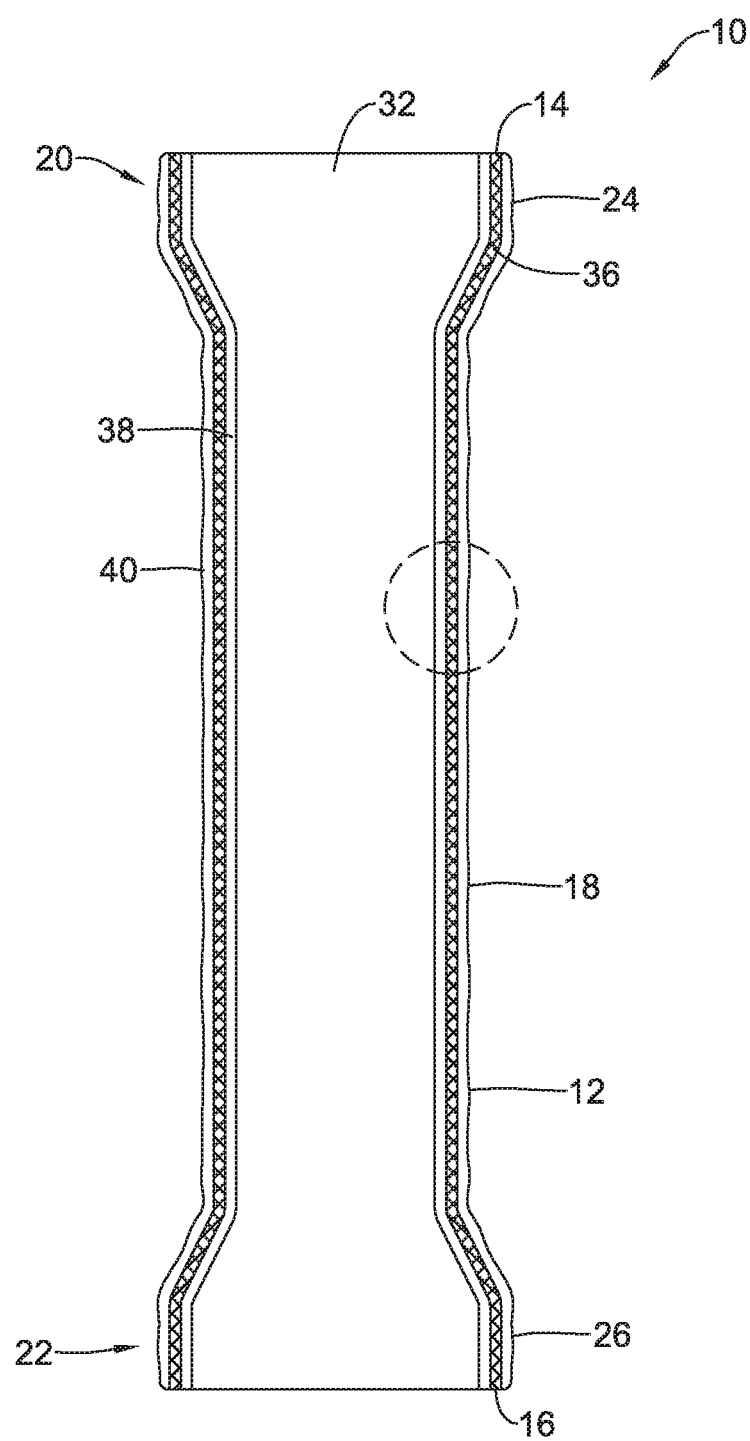
FIG. 2 is a cross-sectional view of the illustrative stent of FIG. 1.

FIG. 1 illustrates a side view of an illustrative endoluminal implant 10, such as, but not limited to, a stent. FIG. 2 illustrates a cross-sectional view of the illustrative stent 10 of FIG. 1, taken at line 2-2. In some instances, the stent 10 may be formed from an elongated tubular member 12. While the stent 10 is described as generally tubular, it is contemplated that the stent 10 may take any cross-sectional shape desired. The stent 10 may have a first, or proximal, end 14, a second, or distal, end 16, and an intermediate region 18 disposed between the first end 14 and the second end 16. The stent 10 may include a lumen 32 extending from a first opening adjacent the first end 14 to a second opening adjacent to the second end 16 to allow for the passage of food, fluids, etc.

The stent 10 may be radially expandable from a first radially collapsed configuration (not explicitly shown) to a second radially expanded configuration, as shown in FIGS. 1 and 2. The stent 10 may be structured to extend across a stricture and to apply a radially outward pressure to the stricture in a lumen to open the lumen and allow for the passage of foods, fluids, air, etc.

The stent 10 may have a scaffold structure, fabricated from a number of filaments or struts 36. The scaffold structure may extend from the first end 14 to the second end 16 of the stent 10. For example, the scaffold structure may extend continuously from the first end 14 to the second end 16 of the stent 10. In some embodiments, the stent 10 may be braided with one filament to form the scaffold structure. In other embodiments, the stent 10 may be braided with several filaments to form the scaffold structure, as is found, for example, in the WallFlex®, WALLSTENT®, and Polyflex® stents, made and distributed by Boston Scientific, Corporation. In another embodiment, the stent 10 may be knitted to form the scaffold structure, such as the Ultraflex™ stents made by Boston Scientific, Corporation. In yet another embodiment, the stent 10 may be of a knotted type, such the Precision Colonic™ stents made by Boston Scientific, Corporation. Thus, in such instances one or more of the filament(s) forming the scaffold structure may extend continuously from the first end 14 to the second end 16 of the stent 10. In still another embodiment, the stent 10 may include a laser cut tubular member to form the scaffold structure, such as the EPIC™ stents made by Boston Scientific, Corporation. A laser cut tubular member may have an open and/or closed cell geometry including one or more interconnected struts formed as a monolithic structure from the tubular member. In such instances, the laser cut tubular member forming the scaffold structure may extend continuously from the first end 14 to the second end 16 of the stent 10.

In some instances, an inner and/or outer surface of the scaffold structure of the stent 10 may be entirely, substantially or partially, covered with a polymeric covering or layer 38, 40 (see, for example, FIG. 2). For example, a covering or coating may help reduce food impaction and/or reduce tumor or tissue ingrowth. In some instances, the inner layer 38 and the outer layer 40 may be formed as a unitary structure. In other embodiments, the inner layer 38 and the outer layer 40 may be formed as separate layers. The inner and outer layers 38, 40 may be formed from the same material or different materials, as desired. The inner layer 38 and/or outer layer 40 may span or be disposed within openings or interstices defined between adjacent stent filaments or struts 36 of the scaffold structure, as more clearly shown in FIG. 3 which illustrates an enlarged view of a portion of the stent 10 shown in dashed lines in FIG. 2. It can be appreciated that as inner layer 38 and outer layer 40 extend outwardly and inwardly, respectively, they may touch and/or form an interface region within the spaces (e.g., openings, cells, interstices) in the wall of the scaffold structure of the stent 10. For example, the detailed view of FIG. 2 shows that both the inner and outer layers 38, 40 may extend into the openings defined between adjacent stent struts 36 and form an interface region. Further, the inner and outer layers 38, 40 may additionally extend between adjacent filaments or struts 36, thereby filling any space between adjacent filament or strut members 36.

It is contemplated that the stent 10 can be made from a number of different materials such as, but not limited to, metals, metal alloys, shape memory alloys and/or polymers, as desired, enabling the stent 10 to be expanded into shape when accurately positioned within the body. In some instances, the material may be selected to enable the stent 10 to be removed with relative ease as well. For example, the stent 10 can be formed from alloys such as, but not limited to, nitinol and Elgiloy®. Depending on the material selected for construction, the stent 10 may be self-expanding or require an external force to expand the stent 10. In some embodiments, filaments may be used to make the stent 10, which may be composite filaments, for example, having an outer shell made of nitinol having a platinum core. It is further contemplated the stent 10 may be formed from polymers including, but not limited to, polyethylene terephthalate (PET).

In some instances, in the expanded configuration, the stent 10 may include a first end region 20 extending to the first end 14 and a second end region 22 extending to the second end 16. In some embodiments, the first end region 20 and the second end region 22 may include flared regions 24, 26 positioned adjacent to the first end 14 and the second end 16 of the stent 10. The flared regions 24, 26 may be configured to engage an interior portion of the walls of the esophagus, although this is not required. In some embodiments, the flared regions 24, 26 may have a larger diameter than an intermediate region 18 of the stent 10 located between the end regions 20, 22 to prevent or help prevent the stent 10 from migrating once placed in the esophagus or other body lumen. It is contemplated that the transition 28, 30 from the cross-sectional area of the intermediate region 18 to the retention features or flared regions 24, 26 may be gradual, sloped, or occur in an abrupt step-wise manner, as desired.

In some embodiments, the first anti-migration flared region 24 may have a first outer diameter and the second anti-migration flared region 26 may have a second outer diameter. The outer diameter of the first anti-migration flared region 24 and/or the second anti-migration flared region 26 may be greater than the outer diameter of the intermediate region 18. In some instances, the first and second outer diameters may be approximately the same, while in other instances, the first and second outer diameters may be different. In some embodiments, the stent 10 may include only one or none of the flared regions 24, 26. For example, the first end region 20 may include a flare 24 while the second end region 22 may have an outer diameter similar to the intermediate region 18. It is further contemplated that the second end region 22 may include a flare 26 while the first end region 20 may have an outer diameter similar to an outer diameter of the intermediate region 18. In some embodiments, the stent 10 may have a uniform outer diameter from the first end 14 to the second end 16. In some embodiments, the outer diameter of the intermediate region 18 may be in the range of 15 to 25 millimeters. The outer diameter of the flares 24, 26 may be in the range of 20 to 30 millimeters. It is contemplated that the outer diameter of the stent 10 may be varied to suit the desired application.

Figure 3:
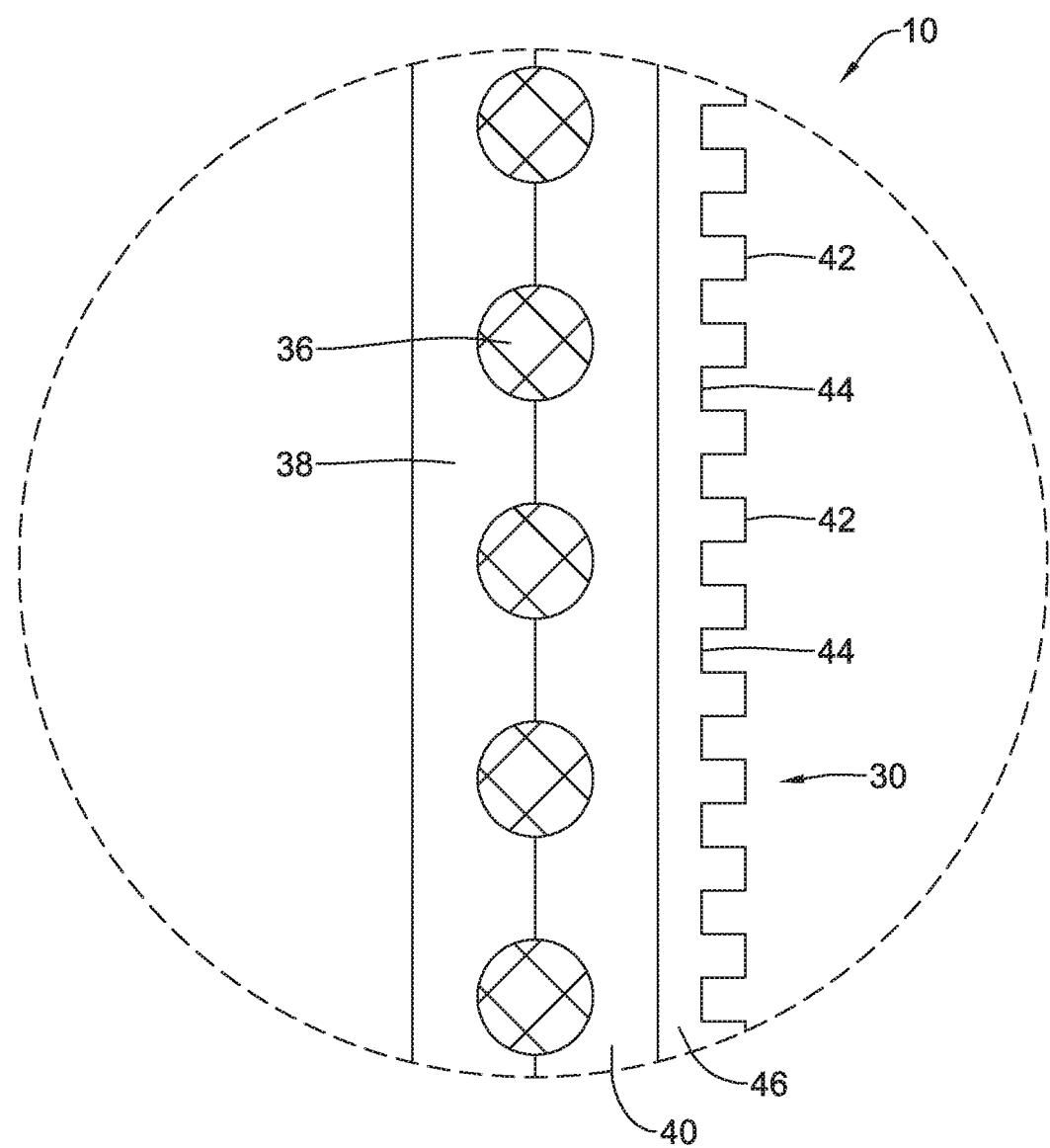
FIG. 3 is an enlarged cross-sectional view of a portion of the illustrative stent of FIG. 2.

As can be seen more clearly in FIG. 3, in some embodiments, the outer surface 28 of the stent 10 may include a micropatterned surface 30 including a plurality of raised micro-pillars or protrusions 42 and recesses 44. The protrusions 42 may have a height, length, and/or width in the range of 1 micrometer (μm) to 1000 μm, for example. It is contemplated that the protrusions 42 may take any cross-sectional shape desired, including, but not limited to square, rectangular, circular, oblong, triangular polygonal, or combinations thereof. While the pattern 30 has been illustrated as a pillar-like pattern, it should be understood the protrusions 42 need not have a constant cross-sectional size or shape from the base to the tip therefor. For example, the protrusions 42 may be pyramidal, hemispherical, or conical in shape. In some embodiments, the protrusions 42 of the micropatterned surface 30 may all have the same shape. In other embodiments, the protrusions 42 of the micropatterned surface 30 may include two or more different shapes depending on the desired response. For example, a portion of the micropatterned surface 30 may include protrusions 42 which encourage cell growth, while another portion of the micropatterned surface 30 may include protrusions 42 which inhibit cell growth. In some cases, the protrusions 42 and/or recesses 44 may be uniformly or evenly distributed about the outer surface stent 10. In other cases, the protrusions 42 and/or recesses 44 may be eccentrically distributed. For example, portions of the stent 10 may be free from the micropatterned surface 30 or the protrusions 42 may vary in density over the outer surface of the stent 10. In some cases, the protrusions 42 may be provided on the flared regions 24, 26 while the intermediate region 18 may be free from the micropatterned surface 30. These are just examples. The protrusions 42 may be present in any number of shape, size and/or distribution combinations desired. For example, The size, spacing, and/or quantity of the protrusions 42 may be varied, as desired, to achieve the desired effect. Some illustrative micropatterns and methods for forming said patterns are described in commonly assigned U.S. Patent Publication Number 2013/0268063, entitled ANTI-MIGRATION MICROPATTERNED STENT COATING, U.S. Patent Publication Number 2014/0277395, entitled ANTI-MIGRATION MICROPATTERNED STENT COATING, U.S. Patent Publication Number 2015/0051693, entitled ANTI-MIGRATION MICROPATTERNED STENT COATING, and U.S. Patent Publication Number 2016/0287416, entitled "METHOD TO CREATE MICROPATTERNS ON AN INSIDE SURFACE OF A STENT," each of which is hereby incorporated by reference.

The micropatterned surface 30 may be formed in a coating or layer 46, for example, but not limited to a silicone layer, disposed on top of the outer layer 40. In other embodiments, the micropatterned surface 30 may be formed in the outer layer 40. In some cases, the micropatterned surface 30 may provide and/or promote controlled tissue ingrowth into the stent coating 46. For example, studies have shown that certain micropatterns on medical devices have an effect on the endothelial cell rate of metallic and polymeric substrates. In some instances, in-vitro tests have demonstrated a difference as high as a factor of five between standard smooth surfaces and micropatterned surfaces. In other cases, the micropatterned surface 30 may inhibit tissue ingrowth.

Figure 4A:
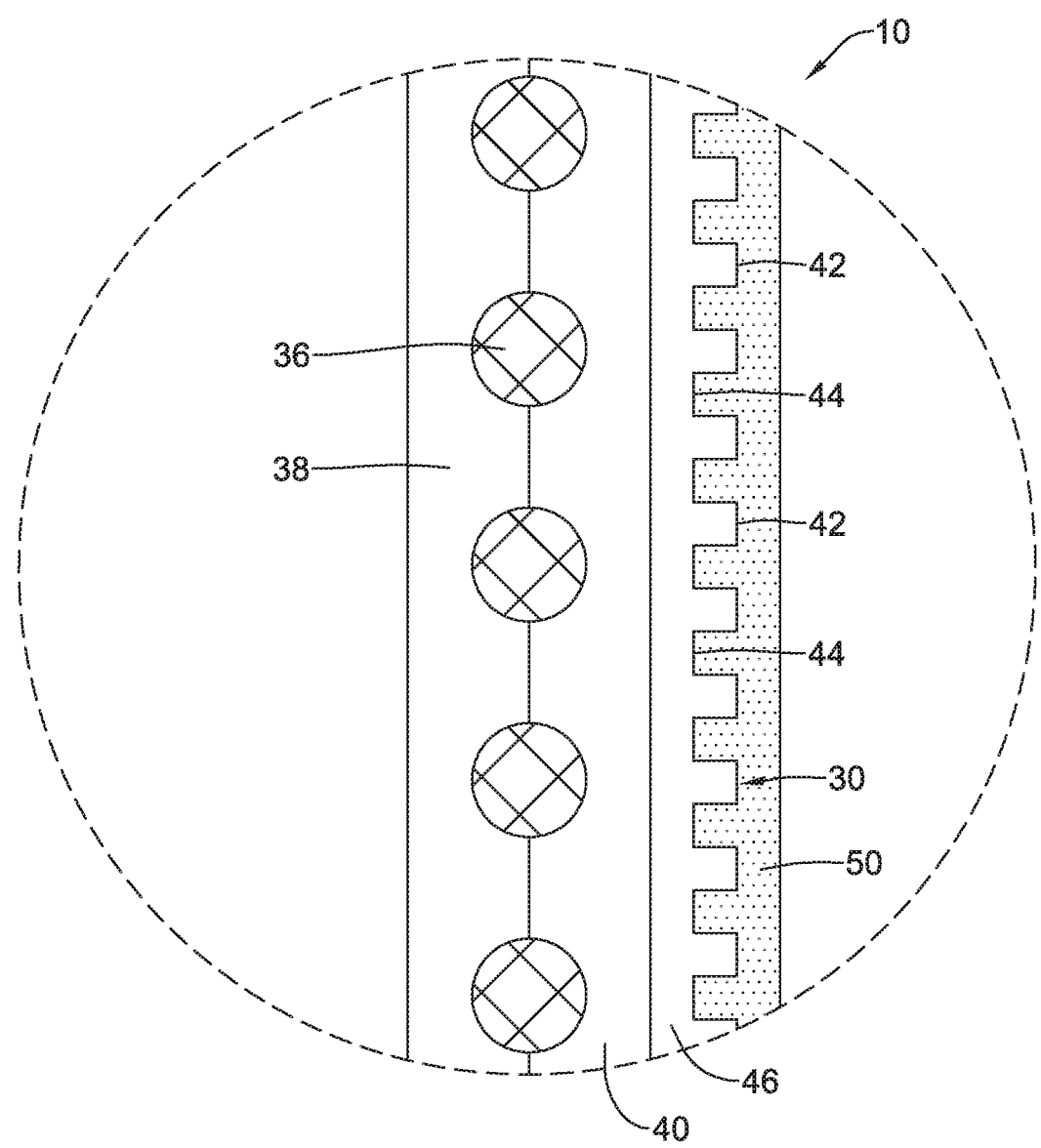
FIGS. 4A-4C are enlarged cross-sectional view of a portion of the illustrative stent of FIG. 2 having a coating thereon.
Figure 4B:
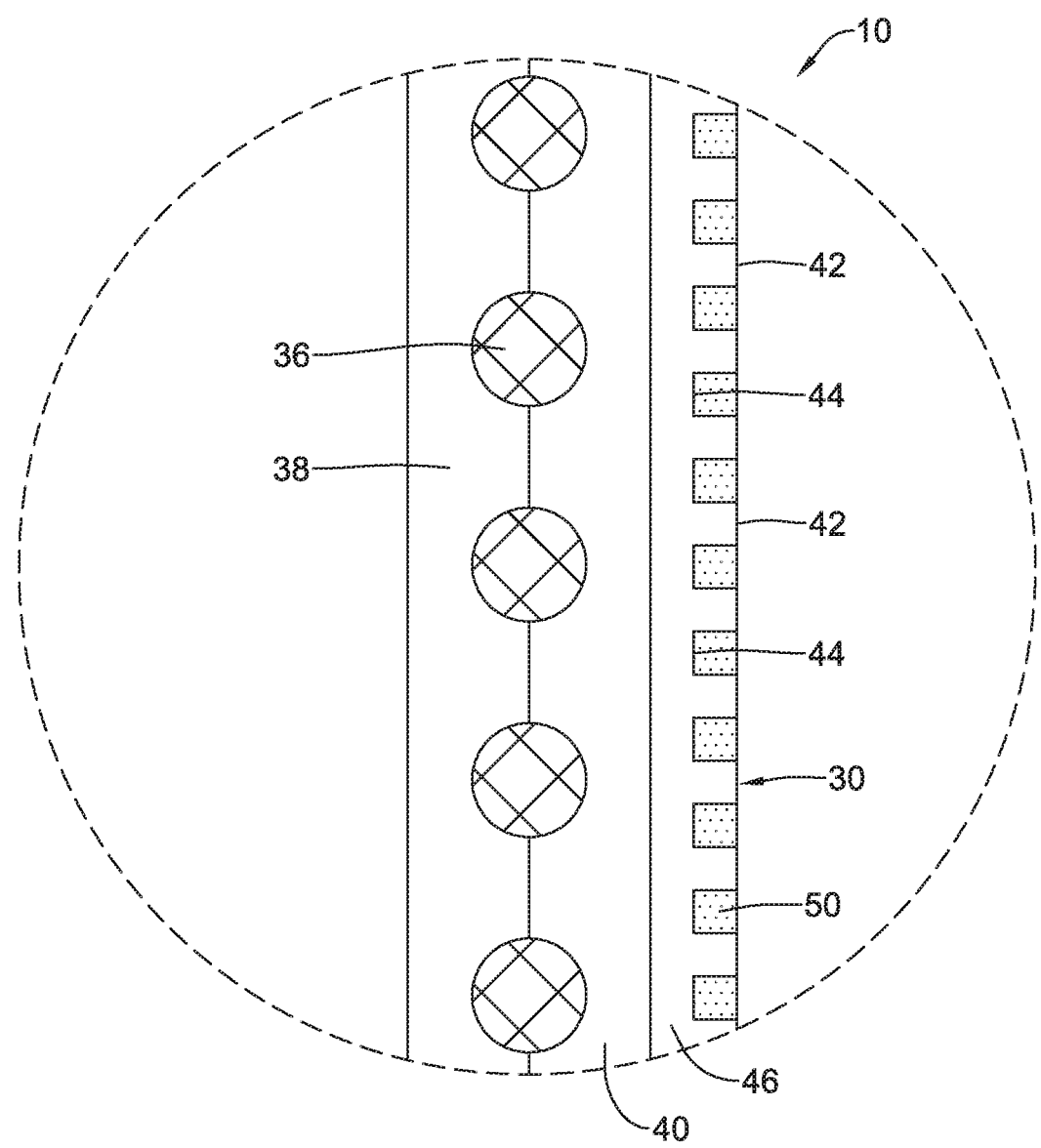
Figure 4C:
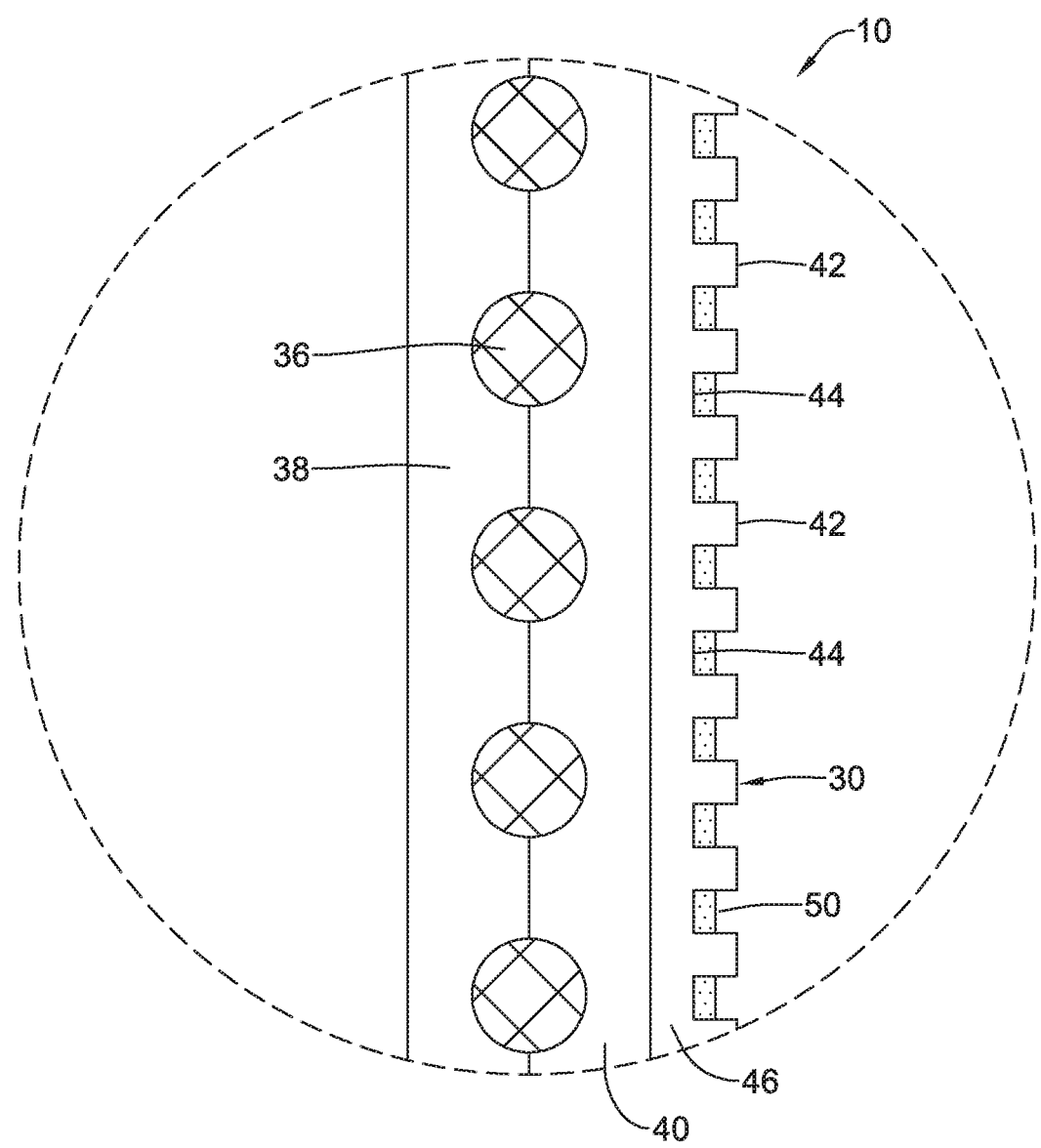

While the micropatterned surface 30 may encourage cell growth into and around the protrusions 42, it is contemplated that it may take some time for the cell growth to fixate the stent 10 to minimize migration. However, as some stent migration occurs soon after implantation (e.g., before tissue ingrowth can occur), it may be desirable to at least temporarily secure the stent 10 through a secondary means. Referring now to FIGS. 4A-4C, which are enlarged cross-sections of a sidewall of the stent 10 including an extracellular matrix (ECM) 50 disposed over the micropatterned surface 30. The ECM layer 50 may act as an adhesive to temporarily secure the stent 10 while also encouraging cell growth, as will be described in more detail herein. As will be described in more detail herein, the ECM layer 50 may be applied as an extracellular matrix hydrogel and allowed to dry into an extracellular matrix.

Extracellular matrix (ECM) is the non-cellular component present within all tissues and organs, and provides not only essential physical scaffolding for the cellular constituents but also initiates crucial biochemical and biomechanical cues that are required for tissue morphogenesis, differentiation and homeostasis. The extracellular matrix is a naturally occurring and necessary structural component present within tissues and organs of living creatures. It comprises the area external to cells and provides physical scaffolding as well as biochemical and biomechanical cues that direct cell function. Essentially, ECM is the glue that holds cells within a tissue together. ECM is composed of water, proteins, and polysaccharides but has a unique composition depending on its purpose in a specific tissue. It is also a highly dynamic structure constantly adapting to fit the requirements of its environment. ECM may contain adhesion molecules to adhere to cells. ECM may be completely bioaborbable ECM may be made into a hydrogel through enzymatic digestion of the ECM to make a liquid form of the material which can then be repolymerized into a gel (e.g., an extracellular matrix hydrogel) or mixed with a synthetic polymer to make a hybrid scaffold. It is contemplated that the ECM 50 may be applied to the micropatterned surface 30 of the stent 10 in a liquid or fluid form (e.g., as a hydrogel). The micropatterned surface 30 may function as a reservoir to hold the liquid ECM 50 in place during application of the gel. It is contemplated that the ECM may be applied to the micropatterned surface 30 at a variety of depths. In one example, the ECM 50 may completely fill the recesses 44 and cover a top surface of the protrusions 42 such that the ECM 50 completely covers or forms a continuous coating over the micropatterned surface 30, as shown in FIG. 4A. In another example, the ECM 50 may fill the recesses 44 such that the ECM 50 forms a generally planar surface with the top surfaces of the protrusions 42, as shown in FIG. 4B. In yet another example, the ECM 50 may be disposed within the recesses 44 such that a height of the ECM 50 is less than a height of the protrusions 42, as shown in FIG. 4C. It should be understood that the thickness of the ECM layer 50 may be any thickness desired.

The micropatterned surface 30 may initially function as a reservoir to hold the ECM 50 in place during application of the gel. As described above, the ECM 50 is adhesive and, as the outermost layer of the stent 10, may act to anchor stent 10 in place after implantation. As the ECM 50 is absorbed, the nutrients may promote cell regeneration and growth. This may cause the tissue adjacent to the stent 10 to grow into the voids 44 in the micropatterned surface 30, thus creating a tissue interlock between the protrusions 42 and the tissue. This tissue interlock combined with the increased surface area that the micropatterned surface 30 provides may increase friction between the tissue and the stent 10 further reducing the risk of migration.

Figure 5:
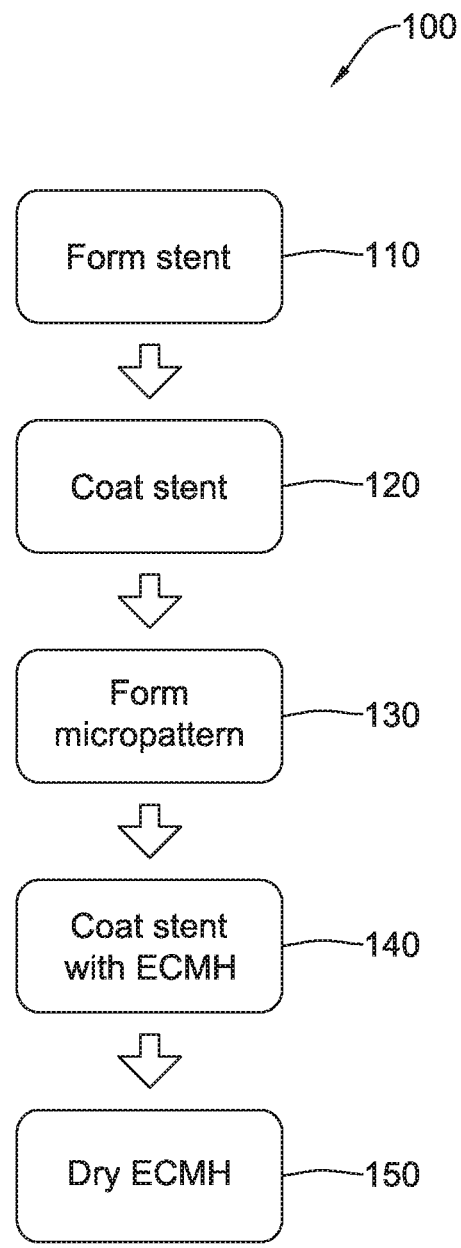
FIG. 5 is an illustrative method of forming a stent.

FIG. 5 is a flow chart of an illustrative method 100 for manufacturing a stent having an extracellular matrix hydrogel coating, such as the stent 10 described above. At step 110, an open cell stent may be braided, woven or laser cut in a traditional manner. The stent may then be coated in a traditional manner for provided a covered stent, as shown at step 120. In some cases, the coating may be a silicone or other polymer covering, although this is not required. The micropattern may then be formed in the stent covering, on the stent covering, or coupled to the stent covering as shown at step 130. In some embodiments, the micropattern may be formed at the same time as the coating is applied to the open cell stent. For example, that the micropattern may be molded directly onto the stent in the form of a continuous coating that encases the stent wires or filaments. In other words, the micropattern may be formed as monolithic structure with the polymeric covering. The micropattern can be cast using a mold such as, but not limited to pour molded, spin molded, and/or injection molded and allowed to cure to form the micropattern. In other embodiments, the micropattern may be formed as a separate layer directly over the covered stent or as a separate component which is subsequently attached to the covered stent. In some cases, the micropattern may be molded into a silicon layer. This layer having the micropattern may then be applied over the covered stent with continuously or discretely applied liquid adhesive. In some cases, the stent, the micropatterned layer and any other layer so provided may each be formed from a bioabsorbable material in order to create an implant that will completely degrade without additional intervention.

Once the outer surface of the stent has been provided with the micropatterned surface, the stent may be coated with an ECMH coating, as shown at step 140. As described above, the ECMH may be a liquid form of an ECM material. The ECMH may be made by lyophilizing a hydrated sheet of an ECM material. The lyophilized sheet may then be ground into a powder. The powder may then be enzymatically digested to make a liquid form of the material which can then be repolymerized into a gel (e.g., an extracellular matrix hydrogel) or mixed with a synthetic polymer to make a hybrid scaffold. The ECMH may be dip coated, roll coated or spray coated onto the outer surface of the stent. The ECMH may have a viscosity similar to water which allows it to flow into the voids or recesses of the micropattern. It is contemplated that masking techniques may be used to selectively apply the ECMH to less than the entire outer surface of the stent. Further, while the coating and the micropatterned layer is described as being disposed on an outer surface the stent, it is contemplated that either or both may be on an inner surface of the stent, as desired. After application of the liquid ECMH, the ECMH may be dried (e.g., using heat and/or time) to form an extracellular matrix gel or extracellular matrix coating (e.g., a coating resistant to flow), as shown at step 150. The ECM coated stent may then be positioned in the desired treatment region. As described above, the ECM may adhere to the cells of the body lumen and act as a mucosal adhesive to prevent or reduce migration of the stent until tissue ingrowth provide an interlock between the stent and the surround tissue. As the ECM breaks down and absorbs into the body, the ECM may encourage and/or promote tissue ingrowth around the micropattern. The controlled tissue ingrowth may provide anti-migration features while allowing the stent to be removed without trauma to the patient.

Figure 6:
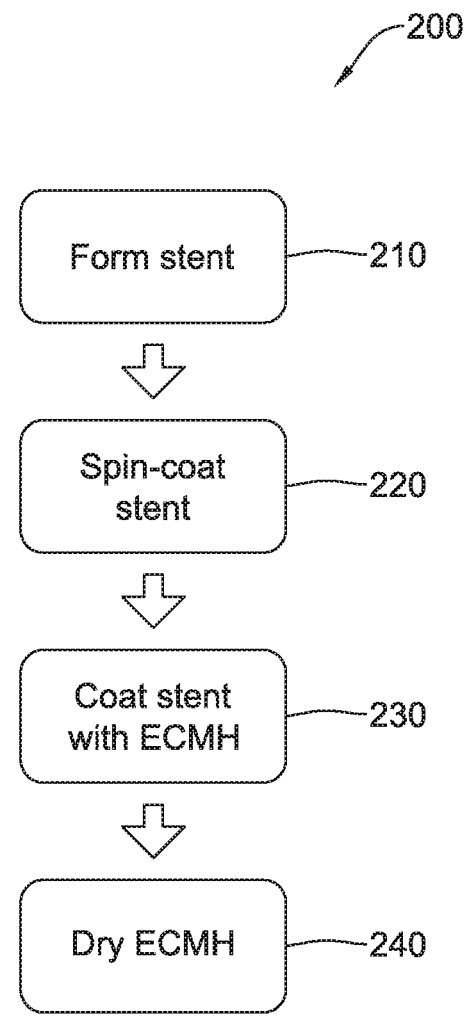
FIG. 6 is another illustrative method of forming a stent.

FIG. 6 illustrates another a flow chart of an illustrative method 200 for manufacturing a stent having an extracellular matrix hydrogel coating. At step 210, an open cell stent may be braided, woven or laser cut in a traditional manner. The stent may then be coated using an electro-spun polymer coating, as shown at step 220. Electro-spinning may provide for a porous coating which prevent tissue in-growth from extending into the lumen of the stent while simultaneously providing a reservoir for receiving an ECM material. It is contemplated the electro-spun coating may be provided in addition to or in place of a traditional stent coating for a covered stent. In some cases, the stent and the electro-spun polymer coating may both be formed from a bioabsorbable material in order to create an implant that will completely degrade without additional intervention. After the electro-spun polymer coating has been applied, the stent may be coated with an ECMH coating, as shown at step 230. As described above, the ECMH may be a liquid form of an ECM material. The ECMH may be made by lyophilizing a hydrated sheet of an ECM material. The lyophilized sheet may then be ground into a powder. The powder may then be enzymatically digested to make a liquid form of the material which can then be repolymerized into a gel (e.g., an extracellular matrix hydrogel) or mixed with a synthetic polymer to make a hybrid scaffold. The ECMH may be dip coated or spray coated onto the outer surface of the stent. The ECMH may have a viscosity similar to water which allows it to flow into the voids or recesses of the electro-spun polymer. It is contemplated that masking techniques may be used to selectively apply the ECMH to less than the entire outer surface of the stent. Further, while the coating and the electro-spun polymer layer is described as being disposed on an outer surface the stent, it is contemplated that either or both may be on an inner surface of the stent, as desired. After application of the liquid ECMH, the ECMH may be dried (e.g., using heat and/or time) to form an extracellular matrix gel or extracellular matrix coating (e.g., a coating resistant to flow), as shown at step 240. The ECM coated stent may then be poisoned in the desired treatment region. As described above, the ECM may adhere to the cells of the body lumen and act as a mucosal adhesive to prevent or reduce migration of the stent until tissue ingrowth provide an interlock between the stent and the surround tissue. As the ECM breaks down and absorbs into the body, the ECM may encourage and/or promote tissue ingrowth around the micropattern. The controlled tissue ingrowth may provide anti-migration features while allowing the stent to be removed without trauma to the patient.

The stents, implants, and the various components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. In some other embodiments, a superelastic alloy, for example a superelastic nitinol can be used to achieve desired properties.

In at least some embodiments, portions or all of the stents or implants may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of the stents or implants in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stents or implants to achieve the same result.

In some embodiments, a degree of Magnetic Resonance Imaging (MM) compatibility is imparted into the stents or implants. For example, the stents implants s or portions thereof, may be made of a material that does not substantially distort the image and create substantial artifacts (i.e., gaps in the image). Certain ferromagnetic materials, for example, may not be suitable because they may create artifacts in an MM image. The stents or implants or portions thereof, may also be made from a material that the Mill machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers for the stents or implants may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Examples of bioabsorbable polymers for the stents or implants may include suitable polymers selected from the following: poly(alpha-hydroxy acid) polymers and copolymers, such as polymers and copolymers of glycolide including polyglycolide (PGA), poly(glycolide-co-lactide) (PGLA), and poly(glycolide-co-trimethylene carbonate (PGA/TMC; polymers and copolymers of polylactide (PLA) including poly-L-lactide (PLLA), poly-D-lactide (PDLA), poly-DL-lactide (PDLLA), poly(lactide-co-tetramethylene glycolide), poly(lactide-co-trimethylene carbonate), poly (lactide-co-delta-valerolactone), polycaprolactone (PCL), poly(lactide-co-epsilon-caprolactone), poly(glycine-co-DL-lactide) and poly(lactide-co-ethylene oxide); polydioxanone polymers such as asymmetrically 3,6-substituted poly-1,4-dioxane-2,5-diones; poly(beta-hydroxybutyrate) (PHBA) and copolymers of the same such as poly(beta-hydroxybutyrate-co-beta-hydroxyvalerate); polygluconate; poly(beta-hydroxypropionate) (PHPA); poly(beta-dioxanone) (PDS); poly(delta-valerolactone); poly(epsilon-caprolactone); methylmethamilate-N-vinylpyrrolidone copolymers; polyester amides; polyesters of oxalic acid; polydihydropyranes; poly(alkyl-2-cyanoacrylate); polyvinyl alcohol (PVA); polypeptides; poly(beta-maleic acid) (PMLA); poly(beta-alkanoic acid); polyethylene oxide (PEO); polyanhydrides, polyphosphoester, and chitin polymers.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An implantable medical device comprising:
   an elongated tubular body having a scaffolding including a plurality of struts forming a plurality of cells defined between adjacent struts;
   a polymeric covering disposed over at least a portion of the elongated tubular body, wherein the covering extends between adj acent struts to fill the cells, wherein the covering includes a plurality of voids formed in an outer surface thereof, the plurality of voids extending through less than an entire thickness of the polymeric covering; and
   an extracellular matrix material coating disposed over the polymeric covering and within the plurality of voids prior to implantation of the implantable medical device within a patient.

2. The implantable medical device of claim 1, wherein the outer surface of the polymeric covering comprises a micropatterned surface including a plurality of protrusions with the plurality of voids defined therebetween.

3. The implantable medical device of claim 2, wherein the plurality of protrusions are formed as a monolithic structure with the polymeric covering.

4. The implantable medical device of claim 2, wherein the polymeric covering includes a first layer and a second layer radially outward of the first layer, the second layer including the micropatterned outer surface having the plurality of protrusions with the plurality of voids defined therebetween.

5. The implantable medical device of claim 4, wherein the second layer is adhesively secured to the first layer.

6. The implantable medical device of claim 4, wherein the first layer extends from a first end to a second end of the elongated tubular body and the second layer extends along less than an entire length of the first layer.

7. The implantable medical device of claim 6, wherein the second layer is disposed over a first region of the first layer adjacent the first end of the elongated tubular body.

8. The implantable medical device claim 7, wherein the second layer is disposed over a second region of the first layer adjacent the second end of the elongated tubular body, with an intermediate portion of the first layer uncovered by the second layer.

9. The implantable medical device of claim 1, wherein the elongated tubular body and the polymeric covering are bioabsorbable.

10. The implantable medical device of claim 1, wherein the extracellular matrix material forms a continuous outer coating over the entire outer surface of the polymeric covering.

11. An implantable medical device comprising:
a stent formed from a plurality of struts forming a plurality of cells defined between adjacent struts;
a polymeric covering disposed over at least a portion of the stent, an inner surface of the covering extending over the struts and filling the cells between adjacent struts, and an outer surface of the covering including a plurality of voids, the plurality of voids extending through less than an entire thickness of the polymeric covering; and
an extracellular matrix material disposed within the plurality of voids prior to implantation of the implantable medical device within a patient.

12. The implantable medical device of claim 11, wherein the outer surface of the polymeric covering comprises a micropatterned surface including a plurality of protrusions with the plurality of voids defined therebetween.

13. The implantable medical device of claim 12, wherein the plurality of protrusions vary in density over the stent.

14. The implantable medical device of claim 11, wherein the stent includes first and second flared end regions with a middle region therebetween, wherein plurality of voids are disposed on the first and second flared end regions and the middle region is free from voids.

15. The implantable medical device of claim 12, wherein the extracellular matrix material completely fills the plurality of voids and covers a top surface of the plurality of protrusions.

16. The implantable medical device of claim 12, wherein the extracellular matrix material fills the plurality of voids but does not cover a top surface of the plurality of protrusions.

17. An implantable medical device comprising:
an elongated tubular body defined by a plurality of struts forming a plurality of cells defined between adjacent struts;
a polymeric covering disposed over at least a portion of the elongated tubular body, wherein the covering extends across the cells wherein the covering includes a plurality of voids formed in an outer surface thereof, the plurality of voids extending through less than an entire thickness of the polymeric covering; and
an extracellular matrix material coating disposed over the polymeric covering prior to implantation of the implantable medical device within a patient.

18. The implantable medical device of claim 17, wherein the outer surface of the polymeric covering comprises a micropatterned outer surface including a plurality of protrusions with the plurality of voids defined therebetween.

19. The implantable medical device of claim 18, wherein the polymeric covering includes a first layer and a second layer radially outward of the first layer, the second layer including the micropatterned outer surface having the plurality of protrusions with the plurality of voids defined therebetween, wherein the first and second layers are different materials.

20. The implantable medical device of claim 17, wherein the elongated tubular body and the polymeric covering are bioabsorbable.

* * * * *